(12) United States Patent
Zhang et al.

(10) Patent No.: US 10,386,334 B2
(45) Date of Patent: Aug. 20, 2019

(54) ION MOBILITY SPECTROMETRY APPARATUS AND METHOD

(71) Applicant: SHIMADZU CORPORATION, Kyoto-shi, Kyoto (JP)

(72) Inventors: Xiaoqiang Zhang, Shanghai (CN); Wenjian Sun, Shanghai (CN)

(73) Assignee: SHIMADZU CORPORATION, Kyoto-Shi, Kyoto (JP)

( * ) Notice: Subject to any disclaimer, the term of this patent is extended or adjusted under 35 U.S.C. 154(b) by 20 days.

(21) Appl. No.: 15/760,445

(22) PCT Filed: Dec. 13, 2016

(86) PCT No.: PCT/JP2016/087123
§ 371 (c)(1),
(2) Date: Mar. 15, 2018

(87) PCT Pub. No.: WO2017/122484
PCT Pub. Date: Jul. 20, 2017

(65) Prior Publication Data
US 2019/0056351 A1  Feb. 21, 2019

(30) Foreign Application Priority Data

Jan. 13, 2016 (CN) .......................... 2016 1 0021240

(51) Int. Cl.
*H01J 49/16* (2006.01)
*H01J 49/40* (2006.01)
(Continued)

(52) U.S. Cl.
CPC .......... *G01N 27/622* (2013.01); *H01J 49/063* (2013.01); *H01J 49/14* (2013.01)

(58) Field of Classification Search
CPC .. H01J 49/0009; H01J 49/0031; H01J 49/063; H01J 49/0072; H01J 49/40; G01N 27/622
See application file for complete search history.

(56) References Cited

U.S. PATENT DOCUMENTS

| 6,107,628 A | 8/2000 | Smith et al. |
| 6,639,213 B2 | 10/2003 | Gillig et al. |

(Continued)

FOREIGN PATENT DOCUMENTS

| WO | 2014195734 A1 | 12/2014 |
| WO | 2014195735 A1 | 12/2014 |

OTHER PUBLICATIONS

International Search Report (ISR) issued by the European Patent Office (EPO) dated Feb. 28, 2017 for PCT/JP20161087123.

(Continued)

*Primary Examiner* — David E Smith
*Assistant Examiner* — Hsien C Tsai
(74) *Attorney, Agent, or Firm* — Tim Tingkang Xia, Esq.; Locke Lord LLP (57) ABSTRACT

An ion mobility spectrometry apparatus and method are provided. The ion mobility spectrometry apparatus includes an ion source for providing ions; an ion guiding device having at least three ends internally communicated: first, second and third guiding ends, wherein ions can enter or exit from the ion guiding device from any ends thereof, the first guiding end is used for entrance of ions provided by the ion source, and the third guiding end is communicated with a downstream device; at least one drift cell in correspondence to the second guiding end, for transmitting ions and/or performing ion mobility analysis, each drift cell having a first and second ends which are internally communicated, wherein the second end of drift cell is communicated with said second guiding end; an ion storage device communicated with said first end of the drift cell, for storing ions or ejecting ions.

28 Claims, 9 Drawing Sheets

(51) Int. Cl.
G01N 27/62 (2006.01)
H01J 49/06 (2006.01)
H01J 49/14 (2006.01)

(56) References Cited

U.S. PATENT DOCUMENTS

| | | |
|---|---|---|
| 2008/0224033 A1 | 9/2008 | Makarov et al. |
| 2009/0014641 A1 | 1/2009 | Bateman et al. |
| 2014/0217278 A1* | 8/2014 | Green .................. H01J 49/062 250/282 |
| 2015/0206731 A1 | 7/2015 | Zhang et al. |
| 2016/0126074 A1* | 5/2016 | Green .................. G01N 27/622 250/282 |

OTHER PUBLICATIONS

Webb, I.K., et al., "Implementation of Dipolar Resonant Excitation for Collision Induced Dissociation with Ion Mobility/Time-of-Flight MS", Journal of the American Society for Mass Spectrometry, vol. 25, Issue 4, pp. 563-571, Published online: Jan. 28, 2014.

* cited by examiner

ION MOBILITY SPECTROMETRY APPARATUS AND METHOD

FIELD OF THE INVENTION

The present invention relates to a mass spectrometer, and more specifically relates to an ion mobility spectrometry apparatus and method.

BACKGROUND OF THE INVENTION

The quadrupole time-of-flight mass spectrometer has become one of dominant commercial mass spectrometers due to its characteristics of speediness, high resolution and mass accuracy, high stability and repeatability. Mass spectrometers are always provided with a gas chromatography or a liquid chromatogram in the front so as to pre-separate a complex sample. In recent years, the coupling between the ion mobility spectrometry technology and mass spectrometry has gained a significant development. Due to the orthogonal separation characteristic for the ion mobility technology and the chromatography technology, the separation capability and peak capacity of the chromatograph-mass spectrometry analysis may be greatly enhanced. A plurality of kinds of ion mobility spectrometry technologies exist currently, wherein a drift cell mobility spectrometry technology under a lower atmosphere pressure (generally 1 torr-4 torr) is widely applied. Its working manner matches well to the modern quadrupole-time of flight mass spectrometer. Therefore, the drift cell-quadrupole-time of flight mass spectrometry almost becomes a standard configuration of a research-level instrument.

The current drift cell—quadrupole-time of flight mass spectrometer, or a drift cell-time of flight mass spectrometer, generally has the following problems, as described in the literature J. Am. Soc. Mass Spectrom. (2014) 25: 563-571: (1) since the resolving power of a drift cell is proportional to the square root of the length, the length of the instrument is usually large to make sure high resolving power, which is not convenient for being used in a common lab; (2) in many cases, e.g., a sample with a very low concentration but relatively simple compositions, the ion mobility separation is not necessary and a mode with only quadrupole-time of flight mass spectrometer is enough. However, in the existing apparatus and method, ions still have to pass through the drift cell; usually, the drift cell has a very low transmission efficiency, causing a significant sensitivity loss; (3) a high drift voltage needs to be applied across the drift cell; therefore, its upstream or downstream devices need a voltage of a higher amplitude so as to drive the ions, which is not only highly demanding on the power supply, but also easily causes electrical breakdown. Therefore, a novel ion mobility spectrometry apparatus and method are desirable to solve the problems above.

SUMMARY OF THE INVENTION

In view of the drawbacks in the prior art, an objective of the present invention is to provide an ion mobility spectrometry apparatus and method, for solving the problem of low ion transmission efficiency caused by the incapability of selecting whether to pass through a drift cell in the prior art.

In order to achieve the above purposes and other related purposes, the present invention provides an ion mobility spectrometry apparatus, comprising: an ion source for providing ions; an ion guiding device comprising: an ion source for providing ions; an ion guiding device comprising: at least three ends internally communicated: a first guiding end, a second guiding end, and a third guiding end, wherein ions can enter or exit from the ion guiding device from any ends thereof, the first guiding end is used for entrance of ions provided by the ion source, and the third guiding end is communicated with a downstream device; at least one drift cell in correspondence to the second guiding end, for transmitting ions and/or performing ion mobility analysis, each drift cell comprising a first end and a second end which are internally communicated, wherein the second end of drift cell is communicated with said second guiding end; an ion storage device communicated with said first end of drift cell, for storing ions or ejecting ions.

In one embodiment of the present invention, the ion guiding device guides ions to enter an drift cell from the second guiding end; the ions, after passing through said drift cell, enter said ion storage device along the first end of drift cell; after a period of time, the ions are ejected from the ion storage device in a pulsed manner; the ions, by passing through said drift cell again, are subject to ion mobility separation, the separated ions enter said ion guiding device again and are guided out to the downstream device from the third guiding end.

In one embodiment of the present invention, the ion guiding device guides ions that are generated from the ion source and enter the ion guiding device to be directly transmitted from the third guiding end to the downstream device, without passing through the drift cell or the ion storage device.

In one embodiment of the present invention, the downstream device comprises: a mass analyzer for mass spectrometry analysis.

In one embodiment of the present invention, the mass analyzer is a time-of-flight mass analyzer.

In one embodiment of the present invention, the downstream device comprises: a quadrupole mass analyzer, a collision cell, and a time-of-flight mass analyzer.

In one embodiment of the present invention, the ion mobility spectrometry apparatus comprises: a detector that is adjacent to the ion storage device, for detecting ions after ion mobility separation during the procedure of being transmitted from the second end of drift cell to the first end of drift cell.

In one embodiment of the present invention, the ion guiding device has a T-shaped structure, and three ends of the T-shaped structure are the first guiding end, the second guiding end and the third guiding end, respectively.

In one embodiment of the present invention, the first guiding end and the third guiding end are two opposite ends at two sides of the T-shaped structure respectively, and the second guiding end is a middle end of the T-shaped structure.

In one embodiment of the present invention, the first guiding end and the second guiding end are two opposite ends at two sides of the T-shaped structure respectively, and the third guiding end is a middle end of the T-shaped structure.

In one embodiment of the present invention, the ion mobility spectrometry apparatus is used for implementing a first function: guiding ions to enter a drift cell from a second guiding end; the ions, after passing through the drift cell, entering an ion storage device along the first end of drift cell, and after a period of time, the ions being ejected from the ion storage device in a pulsed manner, the ejected ions being subject to ion mobility separation by passing through the drift cell, the separated ions entering the ion guiding device and being guided out from the third guiding end to the downstream device; the ion mobility spectrometry apparatus is used for implementing a second function: ions generated from the ion source and entering the ion guiding device being directly transmitted to the downstream device from the third guiding end; wherein the first function and the second function are alternately performed.

In one embodiment of the present invention, there are at least two ion guiding devices that are directly or indirectly communicated.

In one embodiment of the present invention, there are at least two corresponding drift cells, wherein one is for ion transmission, while the other is for ion mobility analysis.

In one embodiment of the present invention, the ion mobility spectrometry apparatus is used for implementing that: ions from the ion source pass through one of the ion guiding device, and enter the ion storage device via the drift cell communicated with the ion guiding device as an ion transmission device; after a period of time, the ions are ejected from the ion storage device and pass through another drift cell as an ion mobility analyzer to be subject to ion mobility separation; the separated ions enter the downstream device through another ion guiding device communicated with the drift cell as the ion mobility analyzer.

In one embodiment of the present invention, the at least two ion guiding devices are communicated with each other via a quadrupole mass analyzer.

In one embodiment of the present invention, the at least two ion guiding devices are communicated with each other via a quadrupole mass analyzer and a collision cell.

In one embodiment of the present invention, the ion mobility spectrometry apparatus is used for implementing that: the ions are selected by the quadrupole mass analyzer to generate parent ions which, after being fragmented in the collision cell, generate daughter ions; the daughter ions enter an drift cell in communication with an outlet end of the collision cell via an ion guiding device, for performing ion mobility separation; the ions within a desired mobility range are selected in the ion storage device and ejected into another drift cell to perform a secondary ion mobility separation for implementing tandem ion mobility spectrometry analysis; wherein said another drift cell is communicated with an inlet end of the quadrupole analyzer via another ion guiding device.

In one embodiment of the present invention, the ion mobility spectrometry apparatus is used for implementing that: each of the drift cells and ion storage devices is used for ion transmission; the ions are selected by the quadrupole mass analyzer to generate parent ions which, after being fragmented in the collision cell, generate daughter ions; the daughter ions, after passing through an ion guiding device, an drift cell, an ion storage device, another ion guiding device, and another drift cell, enter again the quadrupole mass analyzer and collision cell, where the ions are selected and fragmented to generate granddaughter ions so as to implement tandem mass spectrometry analyses.

In order to achieve the above purposes and other related purposes, the present invention provides an ion mobility spectrometry method, comprising: generating ions by an ion source; guiding the ions by an ion guiding device, wherein the ion guiding device comprises: at least three ends communicated internally: a first guiding end, a second guiding end, and a third guiding end, wherein the ions can enter or exit from the ion guiding device from any ends thereof; the first guiding end is used for entrance of the ions provided by the ion source; the third guiding end is communicated with a downstream device; transmitting the ions and/or performing ion mobility analysis by at least one drift cell in correspondence with the second guiding end, wherein each drift cell comprises a first end and a second end that are internally communicated; the second end of drift cell is communicated with said second guiding end; storing or ejecting ions by the ion storage device, wherein the ion storage device is communicated with the first end of drift cell.

In one embodiment of the present invention, the ion mobility spectrometry method comprises: guiding ions, by the ion guiding device, from the second guiding end to enter a communicated drift cell; the ions, after passing through the drift cell, entering the ion storage device along the first end of drift cell of the drift cell; after a period of time, ejecting the ions from the ion storage device in a pulsed manner; the ejected ions being subject to ion mobility separation through the drift cell; the separated ions entering the ion guiding device and being transmitted to the downstream device from the third guiding end.

In one embodiment of the present invention, the ion mobility spectrometry method comprises: guiding, by the ion guiding device, ions generated from the ion source and entering the ion guiding device to be directly transmitted to the downstream device from the third guiding end, without passing through the drift cell or the ion storage device.

In one embodiment of the present invention, the ion mobility spectrometry method comprises: alternatively performing a first function and a second function by the ion mobility spectrometry apparatus; wherein the first function comprises: guiding the ions from the second guiding end to enter a communicated drift cell, the ions, after passing through the drift cell, entering the ion storage device along the first end of drift cell of the drift cell; after a period of time, the ions being ejected from the ion storage device in a pulsed manner, and the ions being subject to ion mobility separation through the drift cell; the separated ions entering the ion guiding device and being transmitted to the downstream device from the third guiding end; the second function comprises: the ions generated from the ion source and entering the ion guiding device being directly transmitted from the third guiding end to the downstream device.

In one embodiment of the present invention, there are at least two ion guiding devices that are directly or indirectly communicated.

In one embodiment of the present invention, there are at least two corresponding drift cells, wherein one is for ion transmission, while the other is for ion mobility analysis.

In one embodiment of the present invention, the ion mobility spectrometry method comprises: causing the ions from the ion source to pass through one of the ion guiding devices, and enter the ion storage device through the drift cell in communication therewith as an ion transmission device; the ions being ejected from the ion storage device and passing through another drift cell as an ion mobility analyzer to implement ion mobility separation, and the separated ions entering the downstream device through another ion guiding device communicated with the drift cell as the ion mobility analyzer.

In one embodiment of the present invention, the at least two ion guiding devices are communicated with each other through a quadrupole mass analyzer and a collision cell.

In one embodiment of the present invention, the ion mobility spectrometry method comprises: selecting ions through the quadrupole mass analyzer to generate parent ions; fragment the parent ions to generate daughter ions through the collision cell; causing the daughter ions to enter an drift cell communicated with an outlet end of the collision cell via an ion guiding device to implement ion mobility separation; selecting ions within a desired mobility range in the ion storage device and ejecting the ions into another drift cell to perform a secondary ion mobility separation for implementing tandem ion mobility spectrometry analysis; wherein said another drift cell is communicated with an inlet end of the quadrupole analyzer via another ion guiding device.

In one embodiment of the present invention, the ion mobility spectrometry method comprises: using each of the drift cells and ion storage devices for ion transmission, and selecting ions through the quadrupole mass analyzer to generate parent ions; fragment the parent ions through the collision cell to generate daughter ions; causing the ions to enter again the quadrupole mass analyzer and the collision cell through an ion guiding device, an drift cell, an ion storage device, another ion guiding device, and another drift cell, and selecting the ions and fragment them to generate granddaughter ions so as to implement tandem mass spectrometry analyses.

As described above, in the ion mobility spectrometry apparatus and method of the present invention, the ion mobility spectrometry apparatus, comprising: an ion source for providing ions; an ion guiding device comprising: at least three ends internally communicated: a first guiding end, a second guiding end, and a third guiding end, wherein ions can enter or exit from the ion guiding device from any ends thereof, the first guiding end is used for entrance of ions provided by the ion source, and the third guiding end is communicated with a downstream device; at least one drift cell in correspondence to the second guiding end, for transmitting ions and/or performing ion mobility analysis, each drift cell comprising a first end and a second end which are internally communicated, wherein the second end of drift cell is communicated with said second guiding end; an ion storage device communicated with said first end of drift cell, for storing ions or ejecting ions. By selecting different ion paths, ion mobility spectrometry analysis may be performed, or direct ion transmission may be performed.

Besides, compared with the prior art, the present invention further has the following advantages during actual use:

1. When the apparatus is coupling with a quadrupole-time of flight mass spectrometer, an longitudinal direction of the drift cell is vertical to the main axis direction of the instrument and is parallel to the longitudinal direction of the flight tube of mass spectrometer; therefore, the length of the instrument still maintains the same as a common quadrupole-time of flight mass spectrometer, while the height only depends on the height of the flight tube of mass spectrometer; hence the size of the instrument will not increase.

2. By switching to a mode in which the quadrupole-time of flight mass spectrometry is used standalone, the ions do not pass through the drift cell, which avoids sensitivity loss; this manner also reduces the ion's dwelling time in the whole ion optics path, which may enhance the analysis speed under certain modes.

3. A high-amplitude voltage is only needed on the drift cell and the ion storage device, while other devices on the upstream and downstream of the drift cell may maintain the original low voltage. Hence not only the power supply device can be simple, but also the electrical breakdown can be effectively avoided.

DETAILED DESCRIPTION OF THE INVENTION

Hereinafter, the preferred embodiments of the present invention will be illustrated through specific examples. A person familiar with this technology may easily understand other advantages and effects through the disclosure in the specification.

Please refer to FIGS. 1-10. It should be known that the structures, scales, and sizes as drawn in the figures are only intended for those skilled in the art to understand and read in conjunction with the content disclosed in the specification, not for limiting conditions that may implement the present invention; therefore, they have no technical substantive meanings; any modifications to the structures, any changes of the proportional relationship or any size adjustments shall fall within the scope that can be covered by the technical contents disclosed in the present invention. Meanwhile, terms such as "upper," "lower," "left," "right," "middle," "one" and the like as quoted in the specification are also only for explicit illustration, not for limiting the scope that is implementable by the present invention. Change or adjustment of their relative relationships should also be regarded as a scope implementable by the present invention without substantively changing the technical content.

Figure 1:
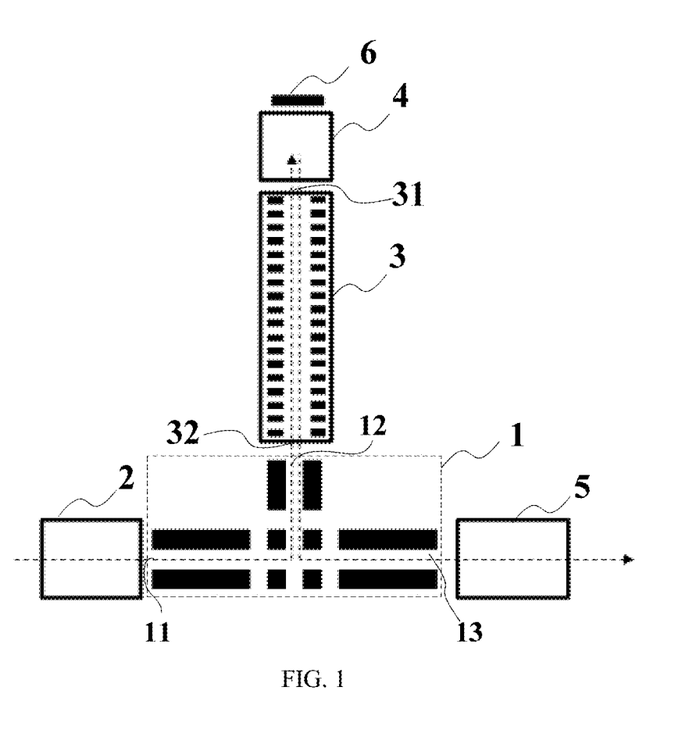
FIG. 1 illustrates a structural diagram of an ion mobility spectrometry apparatus in an example of the first embodiment of the present invention.

As illustrated in FIG. 1, in which a structural diagram of an example of an ion mobility spectrometry apparatus in the first embodiment of the present invention is presented, wherein 1 denotes an ion guiding device, which is preferably the segmented multipole rods which have three ends (e.g., a first guiding end 11, a second guiding end 12, and a third guiding end 13) as an ion inlet or outlet; the ion guiding device is preferably of a T-shaped structure. The first guiding end 11 is interfaced with an ion source 2. The ion source 2 may directly generate ions, e.g., an atmosphere electrospray ionization source (ESI), an electron impact ion source (EI), etc. The third guiding end 13 is interfaced with a downstream device 5; the downstream device 5 may be a mass analyzer or a downstream ion guiding device, and is preferably a quadrupole time-of-flight mass spectrometer. The second guiding end 12 is interfaced with a drift cell 3. The drift cell 3 has two ends defined as a second end of drift cell 32 interfaced with the second guiding end 12 and a first end of drift cell 31 opposite thereto, and the first end of drift cell 31 is interfaced with ion storage device 4.

The apparatus in the present embodiment has at least two working modes between which fast switching is enabled. The first mode is a mobility analysis mode, while the second mode is a non-mobility analysis mode, or referred to as a direct transmission mode.

In the first mode, ions (generally referred to as continuous ion current) generated from the ion source 2 enter the guiding device 1 through the first guiding end 11, are deflected at a middle position of the ion guiding device 1, leave the ion guiding device 1 from the second guiding device end 12, and enter the drift cell 3 from the second end of drift cell 32. At this point, the drift cell 3 is only used for ion transmission; the continuous ion current enters into the ion storage device 4 from the first end of drift cell 31. In the ion storage device, the ions are trapped and stored. After a period of time, an ion gate of the ion storage device 4 adjacent to at the first end of drift cell 31 is closed (a manner of implementing the ion gate will be illustrated infra). Preferably, the remaining ions in the drift cell 3 are cleared; then, the ion gate proximate to the first end of drift cell 31 is opened to eject the ions from the storage device 4 into the drift cell 3 in a pulsed manner. The ions are separated according to mobility in the drift cell 3. The separated ions re-enter the ion guiding device 1 through the second end of drift cell 32 and the second guiding end 12, and are deflected for 90° at a central position; and enter the downstream device 5 along the third guiding end 5, so as to be subject to mass analysis.

In the second mode, ions generated from the ion source 2 enter the ion guiding device 1 through the first guiding end 11, without being deflected; instead, directly enter the downstream device 1 from the third guiding end 13, to be subject to mass analysis or further subject to ion guidance. This mode does not go through the drift cell 3 or ion storage device 4. On one hand, loss of ions within the drift cell is avoided, such that a very high sensitivity may be achieved; secondly, dwelling time of ions is reduced. In some analysis modes, e.g., in a fast polarity switching mode, a very high analysis speed may be obtained.

In the first mode, in order to enhance the utilization efficiency of ions, the step of clearing ions may not be performed; instead, through an operation of the ion gate, the ions that are temporarily not used will be stored. In this case, the continuous ion current enters into the ion storage device 4 through the drift cell; after a period of time, an electric potential of the first guiding end 11 is raised. The ions at the ion source are blocked before the first guiding end 11 and are temporarily stored; after a period of time, after all of the ions in the ion guiding device 1 and the drift cell 3 enter the ion storage device 4, the ion gate of the ion storage device 4 is closed; then, ions of the ion storage device 4 are ejected to be subject to mobility analysis; after all of the ions pass through the third guiding end 13 or after the whole analysis period is completed, the electric potential of the first guiding end 11 is restored, and ions are normally transmitted to start a next analysis period. In this way, the utilization efficiency of the ions is approximate 100%. In order to enhance the transmission efficiency of ions in the drift cell 3, a radio frequency electrical field may be applied. It should be noted that the radio frequency electrical field generally plays a role of heating the ions, such that it will limit the resolution. A periodic focusing direct-current electrical field similar to what is disclosed in the U.S. Pat. No. 6,639,213 may be preferably used, which has an ion transmission efficiency of nearly 100%, and meanwhile, a higher mobility spectrometry resolution is ensured.

The embodiment above may also comprise a detector 6 that is disposed at one side of the ion storage device 4 and the detector 6 may be selectively communicated with the ion storage device 4 at the drift cell 3. If the detector has an aperture in the middle, the detector 6 may also be disposed at the first end of drift cell 31 of the drift cell 3. In another mode, the ions generated from the ion source 2 enter into the drift cell 3 from the second guiding end 12 of the ion guiding device 1 in a pulsed manner, reaching the detector 6 for detection. In this way, the ion mobility analysis may be directly performed.

Figure 2:
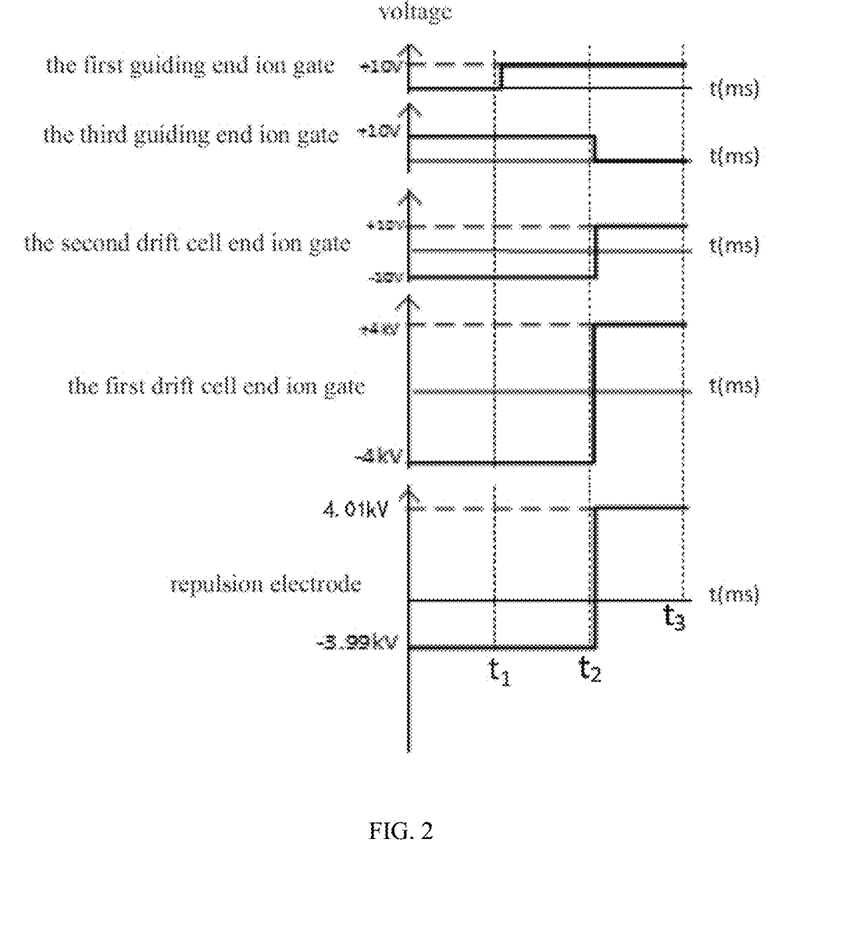
FIG. 2 illustrates a voltage-time sequence diagram of an ion mobility spectrometry apparatus within a typical analysis period in an example according to the first embodiment of the present invention.

In the first mode of the embodiment, a typical voltage-time sequence is illustrated in FIG. 2. The ion gates in the figure are disposed at respective ends above. Its structure may be an aperture lens or the grid electrodes which are well-known in the industry. In the figure, the repulsion electrode is an electrode in the ion storage device 4 and may be disposed adjacent to 6 in FIG. 1. Its structure may be an aperture electrode or a plate electrode. 0-t1 represent a procedure in which ions enter the ion guiding device 1 from the ion source 2 and then enter the ion storage device 4 through the drift cell 3. At time t1, the ion gate of the first guiding end 11 is closed; t1-t2 denote a procedure in which ions remaining in device 1 and 3 enter the ion storage device 4; at time t2, the ion gate of the first end of drift cell 31 is opened for mobility analysis.

The drift cell needs to be applied with thousands or higher of drift voltages so as to reach a higher resolution. In a general drift cell-quadrupole-time-of-flight mass spectrometry, the voltage at the upstream or downstream device of the drift cell needs to be raised therewith. For example, the voltage of the upstream electrospray ion source may reach up to 10,000 voltages, such that the instrument is easily damaged due to occurrence of voltage breakdown. However, in the first mode of the present invention, the parts that need to be applied with high voltages only include the first end of drift cell of the drift cell 3 and the ion storage device 4. The high voltage at these parts needs a fast switching so as to complete the voltage time sequence. However, in the ion source 2, ion guiding device 1, and downstream device 5, a high voltage is not needed. Therefore, other devices at the front and back stages do not need a raised high voltage. In the second mode, since it does not need to use the drift cell 3 or the ion storage device 4, it does not need to apply a high voltage either.

The first mode (i.e., mobility analysis mode) and the second mode (i.e., direct transmission mode) described above may be performed alternatively. For example, within the same chromatographic elution peak, after the mobility analysis mode is performed once, the direct transmission mode will be performed again; and the cycle goes on. Or, a certain overlapping time exists between the two modes, e.g., in the mobility analysis mode, the ions enter the drift cell 3 from the ion guiding device 1; during the time of waiting for the ions to completely enter the ion storage device 4 through the drift cell 3, the T-shaped ion guiding device 1 is switched to the direct transmission mode. The ions that are directly transmitted may be subject to mass spectrometry analysis at a downstream device 5; after the ions in the ion storage device 4 are completely cooled and before preparing for mobility analysis, the ion guiding device 1 is switched back to the mobility analysis mode so as to wait for mobility analysis, and the cycle goes on.

Figure 3A:
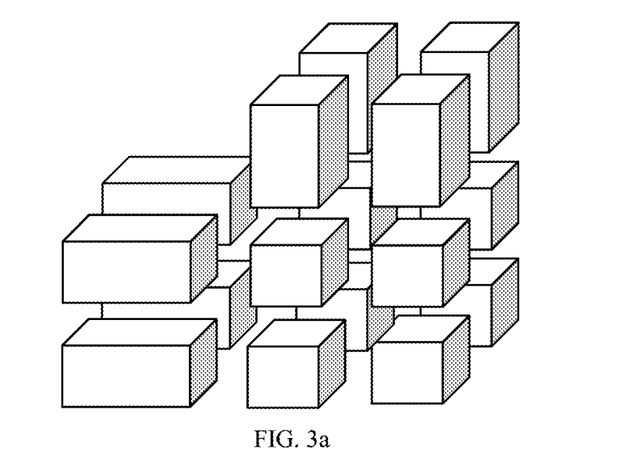
FIGS. 3a and 3b illustrate a structural diagram of two embodiments implemented by an ion guiding device in the first embodiment of the present invention.
Figure 3B:
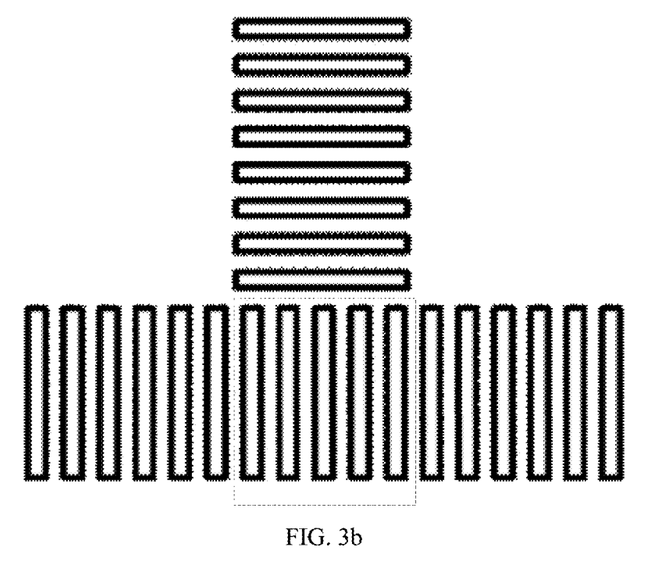
Figure 3C:
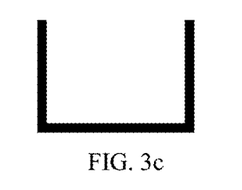
FIG. 3c illustrates a side view structural diagram of part of electrode in FIG. 3b.

FIGS. 3a and 3b illustrate two examples of the ion guiding device in the first embodiment of the present invention. FIG. 3 shows a segmented quadrupole ion guide, which, in actuality, may also use other multipole forms such as hexapole or octapole, etc.; FIG. 3b shows a rectangular electrode array; in actuality, it may also use round and other shapes of electrodes; FIG. 3c illustrates a left or right view of the dummy-block part of electrode in FIG. 3b, which has an upward opening, while the other electrodes may be square in side view. Additionally, the T-shaped ion guiding device is only an exemplary manner; actually, an L-shaped or Y-shaped guiding device that has three ends may also be used; a typical work gas pressure of the ion guiding device is 0.01 torr-10 torr, preferably a gas pressure identical to the drift cell 3, i.e., 1 torr-4 torr.

Figure 4A:
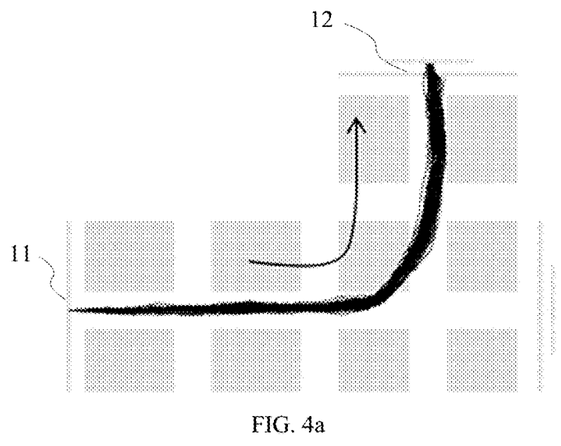
FIGS. 4a and 4b illustrate the ion trajectories by simulation in an ion guiding device under a mobility analysis mode in the first embodiment of the present invention.
Figure 4B:
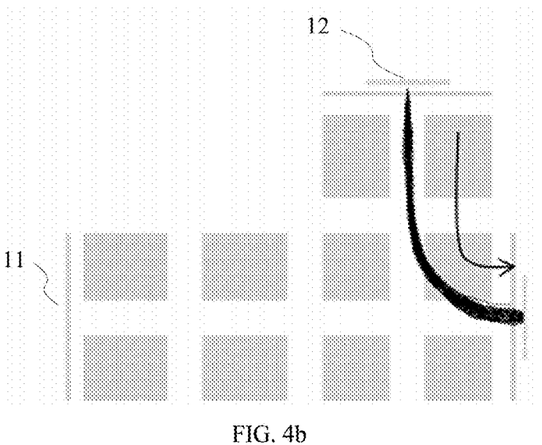
Figure 4C:
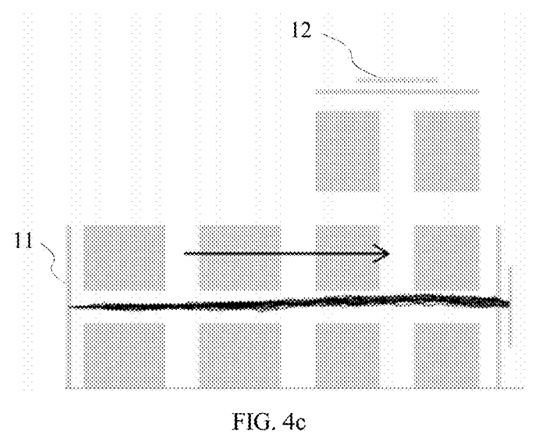
FIG. 4c illustrates the ion trajectories by simulation in an ion guiding device under a direct ion transmission mode in the first embodiment of the present invention.

FIG. 4a-4c illustrate the ion trajectories by simulation in the ion guiding device under the first work mode; wherein FIG. 4a illustrates the ion trajectories from the ion source 2, through the first guiding end 11 of the ion guiding device 1 to the second guiding end 12, to the drift cell 3; FIG. 4b illustrates the ion trajectories for ions returning to the ion guiding device 1 from the drift cell 3 via the second guiding end 12, and then entering the downstream device 5 from the third guiding end 13; FIG. 4c illustrates the ion trajectories for ions that, after flowing through the first guiding end 11 of the ion guiding device 1, directly enter the downstream device 5 from the third guiding end 13. The gas pressure in the simulation is 1 torr, and the mass of the ions is 500. In all the above three cases, the ion transmission efficiency reaches 100%.

Figure 5A:
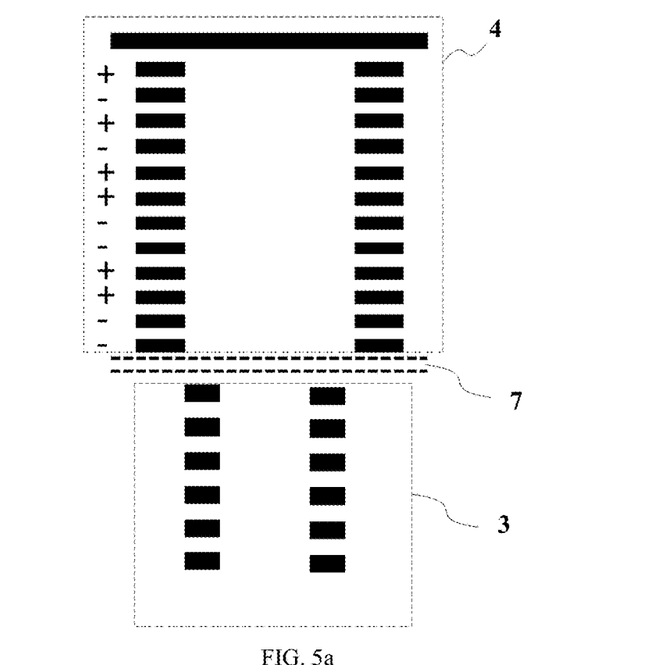
FIGS. 5a-5c illustrate a structural diagram of three examples of an ion storage device in the first embodiment of the present invention.
Figure 5B:
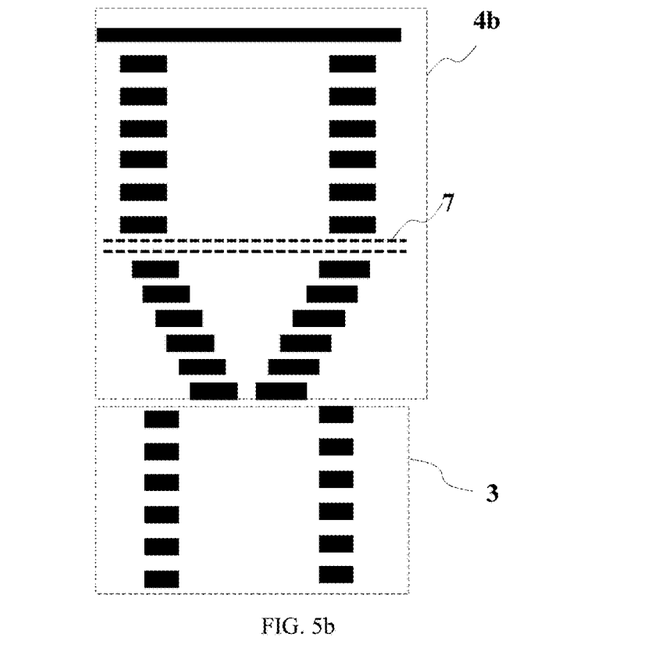
Figure 5C:
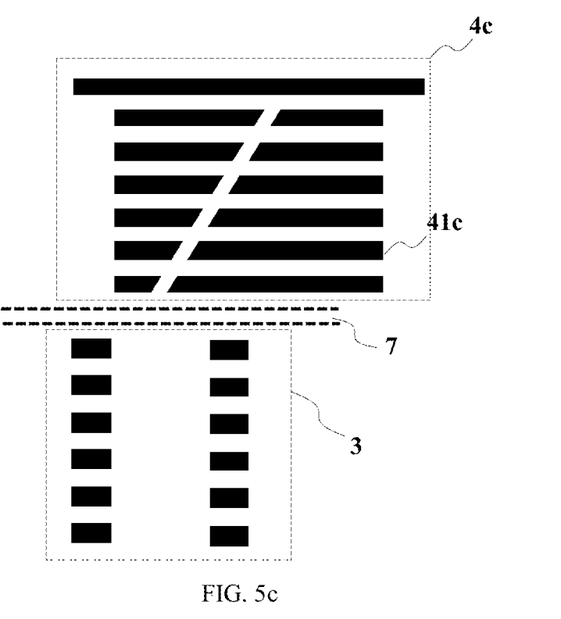
Figure 5D:
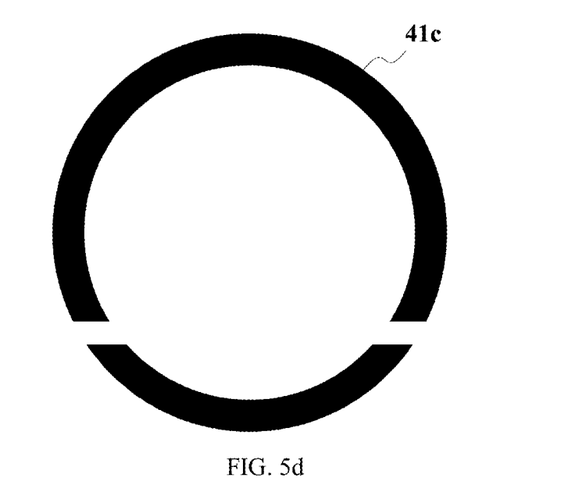
FIG. 5d shows a structural diagram of a ring electrode in the example of FIG. 5c.

FIGS. 5a-5c are three examples of the ion storage device in a first embodiment of the present invention. The ion storage device is required to have a higher ion storage capacity and a higher ion ejection efficiency. In the three embodiments, a dual-layer grid electrode 7 is used as an ion gate. The dual-layer grid electrode has an advantage that mutual influence between the electrical field within the ion storage device and the electric field within the drift cell may be effectively reduced; moreover, the ions may be as close to the grid electrode 7 as possible when being stored, thereby reducing an axial expansion width of the ejected ion beam. All of the three examples adopt the form of an array of stacked-ring electrodes. This form has a higher ion storage capacity. A radio frequency electrical field is applied on the electrode so as to efficiently confine and store the ions. However, when the ions are ejected, a different focusing manner is adopted. Wherein, FIG. 5a is a cross-sectional schematic diagram of the electrode of the ion storage device 4a in the n axial direction. In the figure, "+" and "−" denote radio frequency voltages with equal amplitudes and opposite phases. In the present embodiment, by changing the number of electrodes of the alternate radio frequency electrical field, the radio frequency potential barrier is very close to the axis of the ion storage device 4a at an exit so as to focus the ions; the ion storage device 4b in FIG. 5b adopts, similar to U.S. Pat. No. 6,107,628, uses a gradually shrinking stacked-ring electrode to focus ions; the ion storage device 4b in FIG. 5c adopts, similar to Patent US20150206731, an ion storage device having a plurality of stacked-ring electrodes 41c; FIG. 5d shows an example of a shape of one stacked-ring electrode 41c therein. Each stacked-ring electrode is divided into two segments by an insulation or a broken part and gradually changes along the axis. A bias voltage is applied between two segments of each stacked-ring electrode 41c so as to achieve an effect of focusing ions. In addition to the forms above, a three-dimensional ion trap, a linear ion trap or an ion trap array and the like, which are well known in the art, may be employed.

Figure 6:
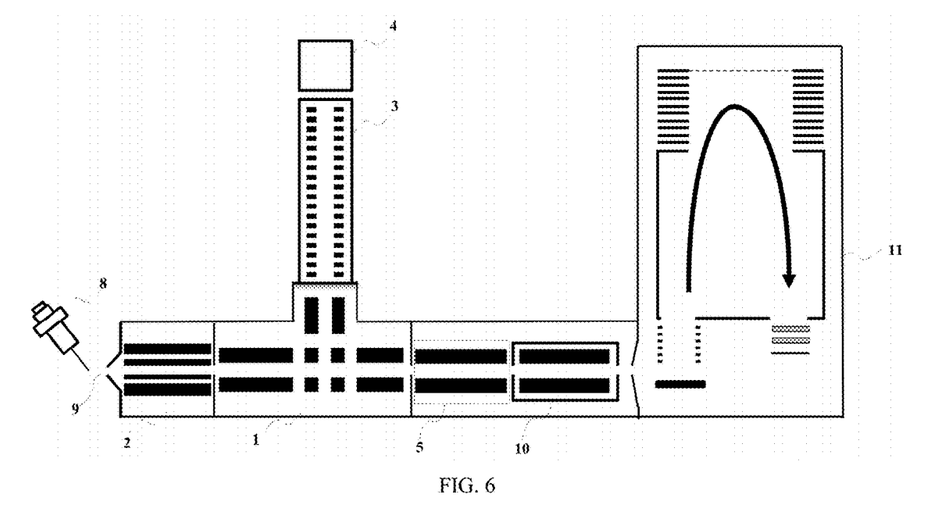
FIG. 6 illustrates an example to coupling an ion mobility spectrometer with a quadrupole time-of-flight mass spectrometer in the first embodiment of the present invention.

FIG. 6 illustrates an example to coupling an ion guiding device to a quadrupole time-of-flight mass spectrometer in the first embodiment of the present invention, wherein 8 is an electrospray ionization source, 9 is an atmosphere pressure interface, 2 is a upstream ion guiding device, 1 is the ion guiding device, 3 is an drift cell, 4 is an ion storage device, 5 is a mass analyzer (which may be a quadrupole) for selecting parent ions, 10 is a collision cell for generating daughter ions, 11 is a time-of-flight mass spectrometer for high-resolution mass analysis for daughter ions. The length of the ion guiding device 1 is very short, e.g., 100 mm, such that the length of the entire apparatus is substantially identical with the length without adding of the drift cell; while the height of the flight mass spectrometer is mainly dependent on the height of the flight tube, e.g., when the flight tube is 1 m, the length of the drift cell 3 may also be close to 1 m. With this length, a very high mobility spectrometry resolution may also be achieved.

Figure 7:
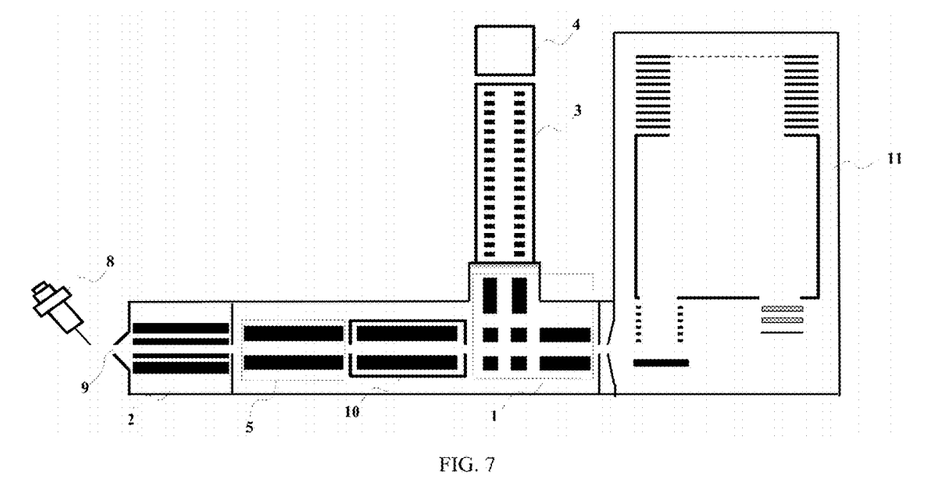
FIG. 7 illustrates another example to coupling an ion mobility spectrometer and a quadrupole time-of-flight mass spectrometer in the first embodiment of the present invention.

FIG. 7 is another example to coupling an ion guiding device to a quadrupole time-of-flight mass spectrometry in the first embodiment of the present invention. In the present example, the ion guiding device 1, relevant drift cell 3, and ion storage device 4 are all disposed downstream to the collision cell 10 and upstream to the time-of-flight mass spectrometer 11. In this way, the daughter ions generated from the collision may be subject to mobility analysis.

Figure 8:
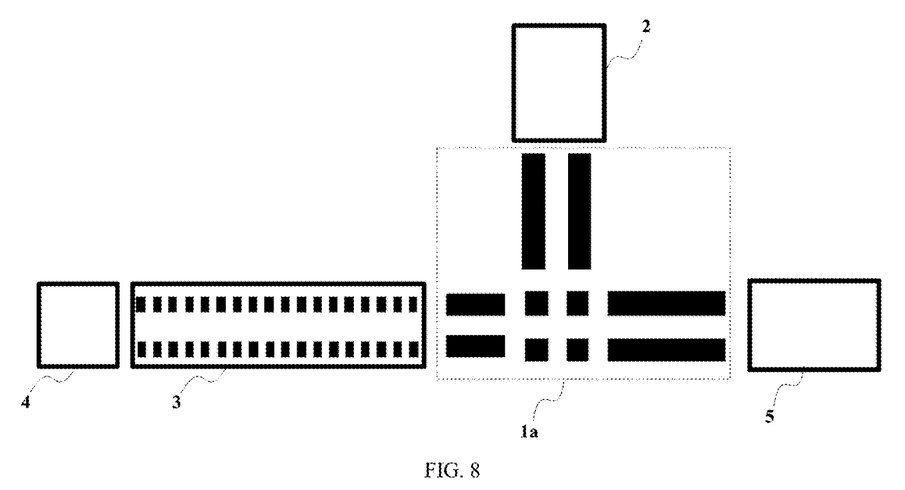
FIG. 8 illustrates a structural diagram of an ion mobility spectrometer in an example according to the second embodiment of the present invention.

FIG. 8 shows one example of a second embodiment of the present invention; compared with the first embodiment, in this embodiment, the positions of the ion source 2 and the drift cell 3 (as well as the attached ion storage device 4) relative to the ion guiding device 1a are exchanged. In this embodiment, in the mobility analysis mode, the ions separated by the drift cell may enter the downstream device 5 without deflection. This avoids resolution loss of the ions potentially due to defection. Therefore, compared with the first embodiment, this embodiment may achieve a higher mobility resolution. However, the length of the instrument in this embodiment will increase correspondingly, but it is still shorter as compared with the traditional manner.

Figure 9:
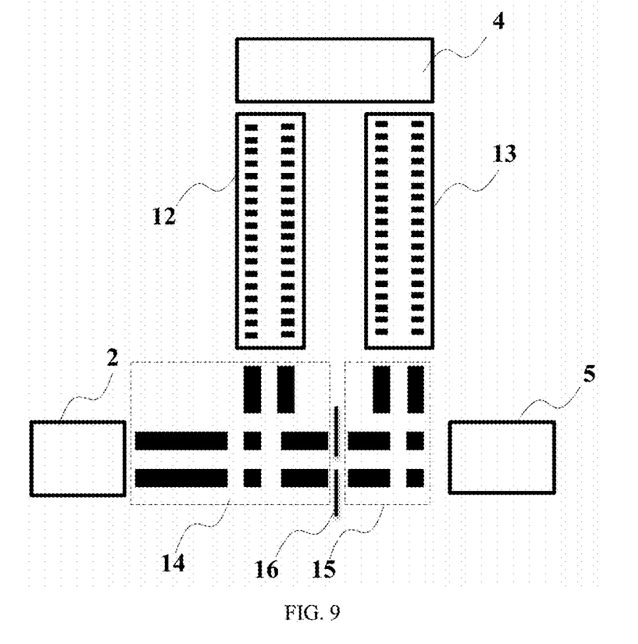
FIG. 9 illustrates a structural diagram of an ion mobility spectrometer in an example according to the third embodiment of the present invention.

FIG. 9 illustrates one example of a third embodiment of the present invention. In the present embodiment, two drift cells 12 and 13 are respectively connected to two second ends of drift cell of the two ion guiding device 14 and 15. Certainly the number is not limited thereto. Wherein, the drift cell 12 is for transmitting ions to the ion storage device 4, which therefore is used for ion guidance. A radio frequency electric field may be applied to enhance the ion transmission efficiency; 13 is a drift cell with a traditional purpose, for ion mobility analysis. In the present embodiment, the inlet and outlet of the ion storage device 4 need to be arranged separately so as to connect two drift cells 12 and 13. Meanwhile, two ion guiding devices 14 and 15 (which may be T-shape or L-shape) are directly connected. A vacuum interface 16 may exist between two ion guiding devices 14 and 15. In this way, they may be under different pressures. The gas pressure of the ion guiding device 14 close to the ion source is substantially consistent with the gas pressure of the two drift cells 12 and 13, while another ion guiding device 15 is in a lower gas pressure. In this case, mobility loss of the ions after being emitted from the drift cells may be effectively avoided.

Figure 10:
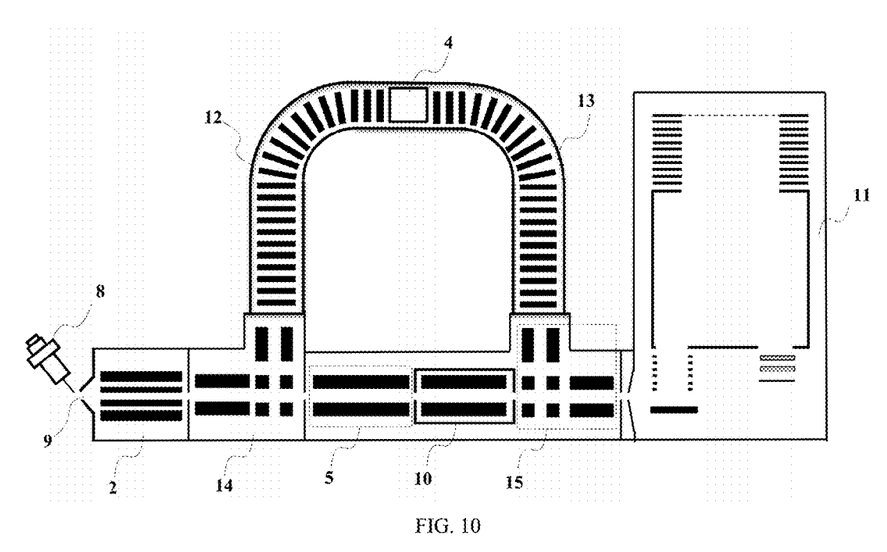
FIG. 10 illustrates a structural diagram of an ion mobility spectrometer in another example of the third embodiment of the present invention.

FIG. 10 illustrates another example of the third embodiment of the present invention. The present example is still an example to coupling the ion mobility spectrometry with the quadrupole time-of-flight mass spectrometer. The present example comprises two ion guiding device 14 and 15, which are connected to two drift cells 12 and 13. Both of the drift cells 12 and 13 may be bent and interfaced via the ion storage device 4. An outlet end of the T-shaped ion guiding device 14 is connected to the mass analyzer 5 for example in a quadrupole type, while an inlet end of the ion guiding device 15 is connected to an outlet of the collision cell 10. In a mobility analysis mode, the ions enter the drift cell 12 from the guiding device 14 for transmission and are stored in the storage device 4, and then return to the drift cell 12 for mobility analysis; and then sequentially enter the mass analyzer 5, the collision cell 10, the ion guiding device 15, the time-of-flight mass spectrometer 10 through the ion guiding device 14, to be subject to tandem mass analysis. In this mode, the drift cell 13 is not used. In another work mode, the drift cell 12 is not used, and the ions are firstly fragmented through the collision cell 10. The daughter ions enter the ion storage device 4 through the ion guiding device 15 and the drift cell 13, and then return to the drift cell 13 for mobility analysis and subsequent time-of-flight mass spectrometry analysis.

In addition to the two modes above, there are also a plurality of combined modes. For example, the drift cells 12 and 13 and the ion storage device 4 are all used for ion transmission. At this time, the ions pass through the ion guiding device 14; parent ions are selected out through the quadrupole analyzer 5 and then enter the collision cell 10 for being fragmented to generate daughter ions; and then sequentially pass through the ion guiding device 15, the drift cell 13, the ion storage device 4, the drift cell 12, ion guiding device 14, and re-enter the mass analyzer 5 to select daughter ions, and then enter the collision cell 10 to generate granddaughter ions. This manner is referred to as an MS3 tandem mass spectrometry analysis, which may even be cycled to perform an MSn tandem mass spectrometry analysis; for another example, the drift cells 12 and 13 may be both used for ion mobility analysis. At this point, the ions may enter the drift cell 13 in a pulsed manner from the ion guiding device 15 to be subject to mobility separation. The ion storage device 4 selects ions in a desired ion mobility range. The ions, after being stored, are ejected into the drift cell 12 for mobility separation. This manner is an IMS-IMS tandem mobility analysis. The above manners may be combined freely, or used alternately and interspersedly, so as to achieve different analytical purposes.

In conjunction with the principle of the above embodiments, the present invention may also provide an ion mobility spectrometry method applied to the apparatus above so as to perform ion mobility analysis and/or other desired analysis.

The embodiments above only exemplarily show the principle and effect of the present invention, not for limiting the present invention. Any person familiar with this technology may modify or alter the embodiments without departing from the spirit and scope of the present invention. Therefore, any equivalent modification or change implemented by those skilled in the art without departing from the spirit and technical idea revealed by the present invention should be covered by the claims of the present invention.

What is claimed is:

1. An ion mobility spectrometry apparatus, comprising:
   an ion source for providing ions;
   an ion guiding device comprising: at least three ends internally communicated: a first guiding end, a second guiding end, and a third guiding end, wherein ions can enter or exit from the ion guiding device from any ends thereof, the first guiding end is used for entrance of ions provided by the ion source, and the third guiding end is communicated with a downstream device;
   at least one drift cell in correspondence to the second guiding end, for transmitting ions and/or performing ion mobility analysis, each drift cell comprising a first end and a second end which are internally communicated, wherein the second end of drift cell is communicated with said second guiding end;
   an ion storage device communicated with said first end of drift cell, for storing ions or ejecting ions.

2. The ion mobility spectrometry apparatus according to claim 1, characterized in that the ion guiding device guides ions to enter an drift cell from the second guiding end; the ions, after passing through said drift cell, enter said ion storage device along the first end of drift cell; after a period of time, the ions are ejected from the ion storage device in a pulsed manner; the ions, by passing through said drift cell again, are subject to ion mobility separation, the separated ions enter said ion guiding device again and are guided out to the downstream device from the third guiding end.

3. The ion mobility spectrometry apparatus according to claim 1, characterized in that the ion guiding device guides ions that are generated from the ion source and enter the ion guiding device to be directly transmitted from the third guiding end to the downstream device, without passing through the drift cell or the ion storage device.

4. The ion mobility spectrometry apparatus according to claim 1, characterized in that the downstream device comprises: a mass analyzer for mass spectrometry analysis.

5. The ion mobility spectrometry apparatus according to claim 4, characterized in that the mass analyzer is a time-of-flight mass analyzer.

6. The ion mobility spectrometry apparatus according to claim 5, characterized in that the downstream device comprises: a quadrupole mass analyzer, a collision cell, and a time-of-flight mass analyzer.

7. The ion mobility spectrometry apparatus according to claim 1, characterized by comprising: a detector that is adjacent to the ion storage device, for detecting ions after ion mobility separation during the procedure of being transmitted from the second end of drift cell to the first end of drift cell.

8. The ion mobility spectrometry apparatus according to claim 1, characterized in that the ion guiding device has a T-shaped structure, and three ends of the T-shaped structure are the first guiding end, the second guiding end and the third guiding end, respectively.

9. The ion mobility spectrometry apparatus according to claim 8, characterized in that the first guiding end and the third guiding end are two opposite ends at two sides of the T-shaped structure respectively, and the second guiding end is a middle end of the T-shaped structure.

10. The ion mobility spectrometry apparatus according to claim 8, characterized in that the first guiding end and the second guiding end are two opposite ends at two sides of the T-shaped structure respectively, and the third guiding end is a middle end of the T-shaped structure.

11. The ion mobility spectrometry apparatus according to claim 1, characterized in that:

the ion mobility spectrometry apparatus is used for implementing a first function: guiding ions to enter a drift cell from a second guiding end; the ions, after passing through the drift cell, entering an ion storage device along the first end of drift cell, and after a period of time, the ions being ejected from the ion storage device in a pulsed manner, the ejected ions being subject to ion mobility separation by passing through the drift cell, the separated ions entering the ion guiding device and being guided out from the third guiding end to the downstream device;

the ion mobility spectrometry apparatus is used for implementing a second function: ions generated from the ion source and entering the ion guiding device being directly transmitted to the downstream device from the third guiding end;

wherein the first function and the second function are alternately performed.

12. The ion mobility spectrometry apparatus according to claim 1, characterized in that there are at least two ion guiding devices that are directly or indirectly communicated.

13. The ion mobility spectrometry apparatus according to claim 12, characterized in that there are at least two corresponding drift cells, wherein one is for ion transmission, while the other is for ion mobility analysis.

14. The ion mobility spectrometry apparatus according to claim 13, characterized in that the ion mobility spectrometry apparatus is used for implementing that: ions from the ion source pass through one of the ion guiding device, and enter the ion storage device via the drift cell communicated with the ion guiding device as an ion transmission device; after a period of time, the ions are ejected from the ion storage device and pass through another drift cell as an ion mobility analyzer to be subject to ion mobility separation; the separated ions enter the downstream device through another ion guiding device communicated with the drift cell as the ion mobility analyzer.

15. The ion mobility spectrometry apparatus according to claim 12, characterized in that the at least two ion guiding devices are communicated with each other via a quadrupole mass analyzer.

16. The ion mobility spectrometry apparatus according to claim 12, characterized in that the at least two ion guiding devices are communicated with each other via a quadrupole mass analyzer and a collision cell.

17. The ion mobility spectrometry apparatus according to claim 16, characterized in that the ion mobility spectrometry apparatus is used for implementing that: the ions are selected by the quadrupole mass analyzer to generate parent ions which, after being fragmented in the collision cell, generate daughter ions; the daughter ions enter an drift cell in communication with an outlet end of the collision cell via an ion guiding device, for performing ion mobility separation; the ions within a desired mobility range are selected in the ion storage device and ejected into another drift cell to perform a secondary ion mobility separation for implementing tandem ion mobility spectrometry analysis; wherein said another drift cell is communicated with an inlet end of the quadrupole analyzer via another ion guiding device.

18. The ion mobility spectrometry apparatus according to claim 16, characterized in that the ion mobility spectrometry apparatus is used for implementing that: each of the drift cells and ion storage devices is used for ion transmission; the ions are selected by the quadrupole mass analyzer to generate parent ions which, after being fragmented in the collision cell, generate daughter ions; the daughter ions, after passing through an ion guiding device, an drift cell, an ion storage device, another ion guiding device, and another drift cell, enter again the quadrupole mass analyzer and collision cell, where the ions are selected and fragmented to generate granddaughter ions so as to implement tandem mass spectrometry analyses.

19. An ion mobility spectrometry method, comprising:

generating ions by an ion source;

guiding the ions by an ion guiding device, wherein the ion guiding device comprises: at least three ends communicated internally: a first guiding end, a second guiding end, and a third guiding end, wherein the ions can enter or exit from the ion guiding device from any ends thereof; the first guiding end is used for entrance of the ions provided by the ion source; the third guiding end is communicated with a downstream device;

transmitting the ions and/or performing ion mobility analysis by at least one drift cell in correspondence with the second guiding end, wherein each drift cell comprises a first end and a second end that are internally communicated; the second end of drift cell is communicated with said second guiding end;

storing or ejecting ions by the ion storage device, wherein the ion storage device is communicated with the first end of drift cell.

20. The ion mobility spectrometry method according to claim 19, comprising:

guiding ions, by the ion guiding device, from the second guiding end to enter a communicated drift cell;

the ions, after passing through the drift cell, entering the ion storage device along the first end of drift cell of the drift cell;

after a period of time, ejecting the ions from the ion storage device in a pulsed manner;

the ejected ions being subject to ion mobility separation through the drift cell; the separated ions entering the ion guiding device and being transmitted to the downstream device from the third guiding end.

21. The ion mobility spectrometry method according to claim 19, comprising:

guiding, by the ion guiding device, ions generated from the ion source and entering the ion guiding device to be directly transmitted to the downstream device from the third guiding end, without passing through the drift cell or the ion storage device.

22. The ion mobility spectrometry method according to claim 19, comprising:

alternatively performing a first function and a second function by the ion mobility spectrometry apparatus; wherein the first function comprises: guiding the ions from the second guiding end to enter a communicated drift cell, the ions, after passing through the drift cell, entering the ion storage device along the first end of drift cell of the drift cell; after a period of time, the ions being ejected from the ion storage device in a pulsed manner, and the ions being subject to ion mobility separation through the drift cell; the separated ions entering the ion guiding device and being transmitted to the downstream device from the third guiding end; the second function comprises: the ions generated from the ion source and entering the ion guiding device being directly transmitted from the third guiding end to the downstream device.

23. The ion mobility spectrometry method according to claim 19, characterized in that: there are at least two ion guiding devices that are directly or indirectly communicated.

24. The ion mobility spectrometry method according to claim 23, characterized in that: there are at least two corresponding drift cells, wherein one is for ion transmission, while the other is for ion mobility analysis.

25. The ion mobility spectrometry method according to claim 24, comprising:
causing the ions from the ion source to pass through one of the ion guiding devices, and enter the ion storage device through the drift cell in communication therewith as an ion transmission device;
the ions being ejected from the ion storage device and passing through another drift cell as an ion mobility analyzer to implement ion mobility separation, and the separated ions entering the downstream device through another ion guiding device communicated with the drift cell as the ion mobility analyzer.

26. The ion mobility spectrometry method according to claim 23, characterized in that the at least two ion guiding devices are communicated with each other through a quadrupole mass analyzer and a collision cell.

27. The ion mobility spectrometry method according to claim 19, comprising:
selecting ions through the quadrupole mass analyzer to generate parent ions;
fragmenting the parent ions to generate daughter ions through the collision cell;
causing the daughter ions to enter an drift cell communicated with an outlet end of the collision cell via an ion guiding device to implement ion mobility separation;
selecting ions within a desired mobility range in the ion storage device and ejecting the ions into another drift cell to perform a secondary ion mobility separation for implementing tandem ion mobility spectrometry analysis; wherein said another drift cell is communicated with an inlet end of the quadrupole analyzer via another ion guiding device.

28. The ion mobility spectrometry method according to claim 26, comprising:
using each of the drift cells and ion storage devices for ion transmission, and selecting ions through the quadrupole mass analyzer to generate parent ions;
fragmenting the parent ions through the collision cell to generate daughter ions;
causing the ions to enter again the quadrupole mass analyzer and the collision cell through an ion guiding device, an drift cell, an ion storage device, another ion guiding device, and another drift cell, and selecting the ions and fragmenting them to generate granddaughter ions so as to implement tandem mass spectrometry analyses.

* * * * *